US010800373B2

(12) United States Patent
Lowe (10) Patent No.: US 10,800,373 B2
(45) Date of Patent: Oct. 13, 2020

(54) VEHICLE SAFETY DEVICES AND HEAT SHIELDS FOR USE AROUND INFLATORS OF AUTOMOTIVE AIRBAG SYSTEMS AND RELATED METHODS

(71) Applicant: Trafalgar Associates, LLC, Vonore, TN (US)

(72) Inventor: Vernon J. Lowe, Greenback, TN (US)

(73) Assignee: Felters of South Carolina, LLC, Roebuck, SC (US)

(*) Notice: Subject to any disclaimer, the term of this patent is extended or adjusted under 35 U.S.C. 154(b) by 53 days.

(21) Appl. No.: 16/212,677

(22) Filed: Dec. 6, 2018

(65) Prior Publication Data
US 2019/0176743 A1 Jun. 13, 2019

Related U.S. Application Data

(60) Provisional application No. 62/595,074, filed on Dec. 6, 2017.

(51) Int. Cl.
| | | |
|---|---|---|
| B60R 21/235 | (2006.01) |
| A61L 2/22 | (2006.01) |
| B02C 11/00 | (2006.01) |
| A61L 2/18 | (2006.01) |
| B02B 1/00 | (2006.01) |
| A23L 3/3508 | (2006.01) |
| A23B 9/26 | (2006.01) |
| A23B 9/30 | (2006.01) |
| B60R 21/2334 | (2011.01) |
| B60R 21/231 | (2011.01) |

(52) U.S. Cl.
CPC .......... *B60R 21/235* (2013.01); *A23B 9/26* (2013.01); *A23B 9/30* (2013.01); *A23L 3/3508* (2013.01); *A61L 2/186* (2013.01); *A61L 2/22* (2013.01); *B02B 1/00* (2013.01); *B02C 11/00* (2013.01); *B60R 21/2334* (2013.01); *A61L 2202/17* (2013.01); *B60R 2021/23123* (2013.01); *B60R 2021/23509* (2013.01); *B60R 2021/23533* (2013.01)

(58) Field of Classification Search
CPC .......... B60R 21/235; B60R 21/2334; B60R 2021/23533; B60R 2021/23509; B60R 2021/23123; A23B 9/30; A23B 9/26; A23L 3/3508; B02C 11/00; B02B 1/00; A61L 2/186; A61L 2/22; A61L 2202/17
See application file for complete search history.

(56) References Cited

U.S. PATENT DOCUMENTS

| | | | | |
|---|---|---|---|---|
| 4,500,593 A | * | 2/1985 | Weber | B32B 15/14 442/200 |
| 2011/0018244 A1 | * | 1/2011 | Schindzielorz | B60R 21/231 280/743.1 |

(Continued)

*Primary Examiner* — Darlene P Condra
(74) *Attorney, Agent, or Firm* — J. Bennett Mullinax, LLC (57) ABSTRACT

Vehicle safety devices, heat shields used in such devices and related methods are provided. The heat shield for use in vehicle airbags can include a woven base substrate and a needlepunched nonwoven substrate comprising silicon-containing fibers. The needlepunched nonwoven can be needlepunched to the woven base substrate such that, when the heat shield is positioned within an interior space of an airbag, the needlepunched nonwoven substrate faces apertures of an inflator within the airbag.

13 Claims, 6 Drawing Sheets

(56) References Cited

U.S. PATENT DOCUMENTS

| | | | |
|---|---|---|---|
| 2011/0316263 A1* | 12/2011 | Lunt | B60R 21/217 |
| | | | 280/730.2 |
| 2014/0340740 A1* | 11/2014 | Saito | G02B 5/26 |
| | | | 359/359 |
| 2015/0056881 A1* | 2/2015 | Zhang | B32B 5/00 |
| | | | 442/268 |
| 2015/0210240 A1* | 7/2015 | Tanaka | D06N 3/0006 |
| | | | 442/189 |
| 2015/0266264 A1* | 9/2015 | Lowe | B32B 5/024 |
| | | | 280/741 |

* cited by examiner

VEHICLE SAFETY DEVICES AND HEAT SHIELDS FOR USE AROUND INFLATORS OF AUTOMOTIVE AIRBAG SYSTEMS AND RELATED METHODS

RELATED APPLICATION

The presently disclosed subject matter claims the benefit of U.S. Provisional Patent Application Ser. No. 62/595,074, filed Dec. 6, 2017, the disclosure of which is incorporated herein by reference in its entirety.

TECHNICAL FIELD

The present subject matter relates to heat shields for use in inflator containers used to house filtration devices and related methods. In particular, the present subject matter relates to heat shields for use in inflator containers used to house filtration devices for use in automotive airbags that can improve the packaging of the inflator and reduce the bulk and size of the heat shield mass/volume surrounding the inflator.

BACKGROUND

An airbag is a vehicle safety device that generally includes a flexible envelope (e.g., a nylon fabric) designed to inflate rapidly during an automobile collision. The airbag's purpose is to cushion occupants during a crash and provide protection to their bodies when they strike interior objects such as the steering wheel, window and/or structural components of the vehicle. Modern vehicles may contain multiple airbags in various side, seat, and/or frontal locations of the passenger and driver seating positions, and sensors may deploy one or more airbags in an impact zone at variable rates based on the type and the severity of impact.

Many airbags are inflated by the ignition of a gas generating propellant via a pyrotechnic device, which rapidly inflates a flexible envelope. The pyrotechnic device usually includes an electrical initiator wrapped in a combustible material and can activate quickly (e.g., less than 2 milliseconds) with a current pulse of about 1 to 3 amperes that are housed in a metal inflator container. When the initiator becomes hot enough, it ignites the combustible material (e.g., a solid propellant). The burning propellant generates inert gas which rapidly expands and inflates the airbag (e.g., the typical rate of inflation in current technology is about 10 to 40 milliseconds). For successful activation, the process requires the pyrotechnic device to generate a high velocity gas that rapidly fills the cushion. The inflation gas will be at high temperature, but relatively low pressure.

A typical combustion gas generant process can include Basic Copper Nitrate ($Cu_2(NO_3)(OH)_3$) (hereinafter "BCN") and Guanidine Nitrate $C(NH_2)_3NO_3$ (hereinafter "GN") and various mineral based oxides. The combustion process generates three typical gas byproducts, water ($H_2O$), carbon dioxide ($CO_2$) and nitrogen ($N_2$). Nitrogen, which generally acts like an inert gas, is used to inflate the air cushion. In addition, the process generates a range of minerals, these minerals can vary. For example, the most significant minerals generated by the process can be Copper bearing minerals. However, the minerals can also include Aluminum (Al), Chloride (Cl), Cyanate compounds, Iron (Fe), Nitrite compounds, Phosphorus (P), Potassium (K), and Titanium (Ti) bearing minerals. These substances occur in a range of particle sizes from microscopic to 1.5 millimeters (mm), and can also reach generant gas temperatures of 700-900° C. just after ignition. Clearly, these extremely hot particulates, if permitted to enter the air cushion, can cause a catastrophic failure. To prevent this, the current technology introduces a filter that also operated as a diffuser at a point prior to where the generant gas jet exits into the air cushion of the fabric bag. The filter is positioned at this point to capture the particulates generated by the combustion reaction and also absorb some of the heat generated by the combustion, thereby lowering the exit gas temperature and the ultimate temperature reached by the airbag. This filter is usually located inside the air cushion inflator device and may take different shapes according to the air cushion size, shape and location in the vehicle. The inflator device can be high temperature pyrotechnic, pyrotechnic hybrid or simply compressed gas activated. The filter is typically a mechanism made of metal with convoluted passages to permit the inflation gas to exit the inflator while collecting particulates within the passages. The gas and particulates transfer heat via conduction and convection to the filter as the gas exits to inflate the cushion.

Despite the use of mechanical filtration devices as described, the combustion particulates and byproducts of the chemical explosion inevitably fail to capture small, high temp particles and the traditional practice is to introduce a textile heat shield to capture the particulate and absorb temperature from the rapidly exiting nitrogen gas. Traditional use of a woven nylon substrate with silicon sacrificial coating is the common practice to resist the impinging shock wave with several layers being added. The number of laminations is dependent upon the power of the inflator to fill the required cushion envelop and design of the associated airbag. The traditional use of a woven nylon substrate with silicon sacrificial coating is the common practice, to resist the impinging shock wave several layers are added, the number of laminations dependent upon the power of the inflator to fill the required cushion envelop and design. The sacrificial coating is destroyed as the gas passes into the heat shield. The sacrificial coating is destroyed as the gas passes into the heat shield. Additionally, to be effective, the woven nylon substrate must be formed into a cushion of a multi lamination wrap that is bulky and difficult to package.

As such a need exists for a heat shield for use in an inflator container of an airbag that house a filtration device that filter the high energy, high temperature gas generant that inflates the airbag where the heat shield provides improved packaging of the inflator and reduce the bulk and size of the heat shield mass/volume surrounding the inflator.

SUMMARY

The present subject matter heat shields for use in inflator containers used to house filtration devices and related methods. In particular, the present subject matter relates to heat shields for use in inflator containers used to house filtration devices for use in automotive airbags that can improve the packaging of the inflator and reduce the bulk and size of the heat shield mass/volume surrounding the inflator. Methods related to the manufacture and use of the heat shields disclosed herein are also provided.

Thus, it is an object of the presently disclosed subject matter to provide heat shields for use in inflator containers of automotive airbags and methods of manufacturing and using such heat shields. While one or more objects of the presently disclosed subject matter having been stated hereinabove, and which can be achieved in whole or in part by the presently disclosed subject matter, other objects will become evident as the description proceeds when taken in connection with the accompanying drawings as best described hereinbelow.

BRIEF DESCRIPTION OF THE DRAWINGS

A full and enabling disclosure of the present subject matter including the best mode thereof to one of ordinary skill in the art is set forth more particularly in the remainder of the specification, including reference to the accompanying figures, in which.

Repeat use of reference characters in the present specification and drawings is intended to represent the same or analogous features or elements of the present subject matter.

DETAILED DESCRIPTION

Reference now will be made to the embodiments of the present subject matter, one or more examples of which are set forth below. Each example is provided by way of an explanation of the present subject matter, not as a limitation. In fact, it will be apparent to those skilled in the art that various modifications and variations can be made in the present subject matter without departing from the scope or spirit of the present subject matter. For instance, features illustrated or described as one embodiment can be used on another embodiment to yield still a further embodiment. Thus, it is intended that the present subject matter cover such modifications and variations as come within the scope of the appended claims and their equivalents. It is to be understood by one of ordinary skill in the art that the present discussion is a description of exemplary embodiments only, and is not intended as limiting the broader aspects of the present subject matter, which broader aspects are embodied in exemplary constructions.

Although the terms first, second, right, left, front, back, etc. may be used herein to describe various features, elements, components, regions, layers and/or sections, these features, elements, components, regions, layers and/or sections should not be limited by these terms. These terms are only used to distinguish one feature, element, component, region, layer or section from another feature, element, component, region, layer or section. Thus, a first feature, element, component, region, layer or section discussed below could be termed a second feature, element, component, region, layer or section without departing from the teachings of the disclosure herein.

Similarly, when a layer is being described in the present disclosure as "on" or "over" another layer or substrate, it is to be understood that the layers can either be directly contacting each other or have another layer or feature between the layers, unless expressly stated to the contrary. Thus, these terms are simply describing the relative position of the layers to each other and do not necessarily mean "on top of" since the relative position above or below depends upon the orientation of the device to the viewer.

Embodiments of the subject matter of the disclosure are described herein with reference to schematic illustrations of embodiments that may be idealized. As such, variations from the shapes and/or positions of features, elements or components within the illustrations as a result of, for example but not limited to, user preferences, manufacturing techniques and/or tolerances are expected. Shapes, sizes and/or positions of features, elements or components illustrated in the figures may also be magnified, minimized, exaggerated, shifted or simplified to facilitate explanation of the subject matter disclosed herein. Thus, the features, elements or components illustrated in the figures are schematic in nature and their shapes and/or positions are not intended to illustrate the precise configuration of the subject matter and are not intended to limit the scope of the subject matter disclosed herein.

It is to be understood that the ranges and limits mentioned herein include all ranges located within the prescribed limits (i.e., subranges). For instance, a range from about 100 to about 200 also includes ranges from 110 to 150, 170 to 190, 153 to 162, and 145.3 to 149.6. Further, a limit of up to about 7 also includes a limit of up to about 5, up to 3, and up to about 4.5, as well as ranges within the limit, such as from about 1 to about 5, and from about 3.2 to about 6.5.

As used herein, the term "polymer" generally includes, but is not limited to, homopolymers; copolymers, such as, for example, block, graft, random and alternating copolymers; and terpolymers; and blends and modifications thereof. Furthermore, unless otherwise specifically limited, the term "polymer" shall include all possible geometrical configurations of the material, including but not limited to metallic polymers and ceramic polymers. These configurations include, but are not limited to isotactic, syndiotactic, and random symmetries.

The term "thermoplastic" is used herein to mean any material formed from a polymer which softens and flows when heated; such a polymer may be heated and softened a number of times without suffering any basic alteration in characteristics, provided heating is below the decomposition temperature of the polymer. Examples of thermoplastic polymers include, by way of illustration only, polyolefins, polyesters, polyamides, polyurethanes, acrylic ester polymers and copolymers, polyvinyl chloride, polyvinyl acetate, etc. and copolymers thereof.

The term "silicon-containing fiber(s)" is used herein to mean fibers that comprise a silicon or silicon compound The present disclosure relates to heat shield materials for use in inflator containers used to house filtration devices and related methods. In particular, the present subject matter relates to heat shields made from heat shield materials for use in inflator containers used to house filtration devices for use in automotive airbags that improve the packaging of the inflator and reduce the bulk and size of the heat shield mass/volume surrounding the inflator that inflates the airbag. More particularly, a heat shield that comprises a nonwoven can be provided. For example, a heat shield can comprise a nonwoven substrate needlepunched to a woven substrate. The nonwoven substrate can comprise a needlepunched web that comprises silicon-containing fibers ("Si") such as silica fibers. The web comprising silicon-containing fibers can also include other thermoplastic polymer fibers that have appropriate properties. For example, in some embodiments, the needlepunched nonwoven web can comprise silicon-containing fibers and polypropylene fibers. In some embodiments, the needlepunched nonwoven web can comprise silicon-containing fibers and polyester fibers, such as PET fibers.

Figure 1:
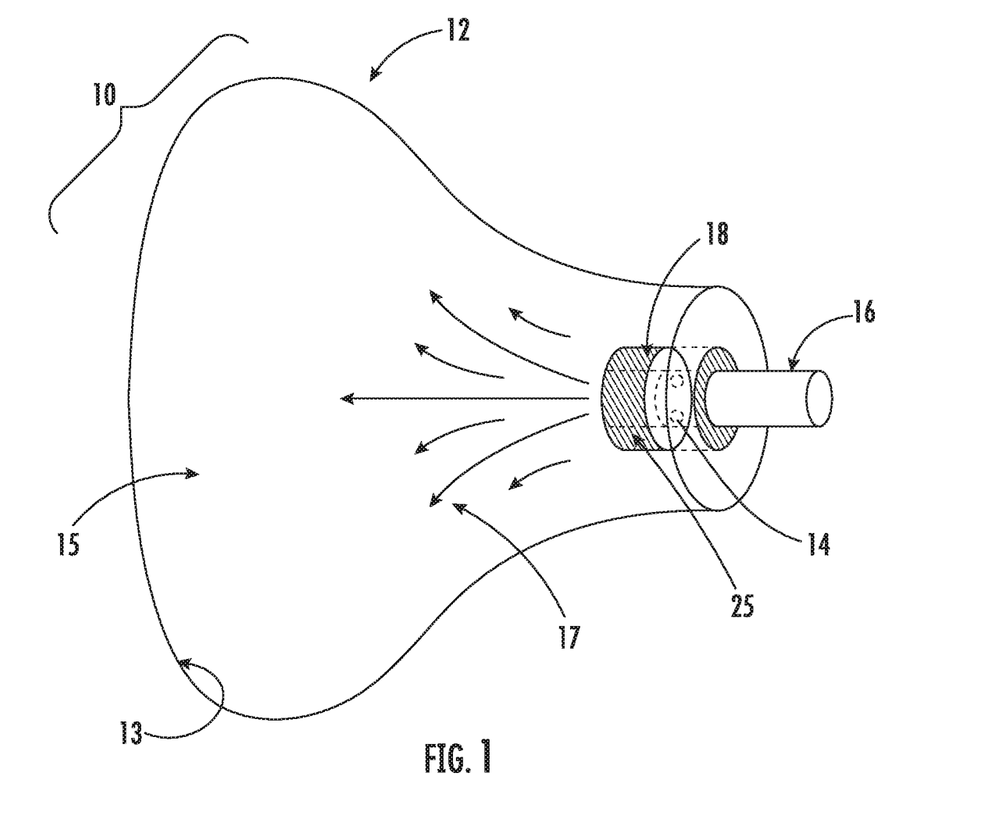
FIG. 1 illustrates a schematic perspective view of an embodiment of a vehicle safety device that employs an embodiment of a heat shield comprising a nonwoven face that comprising silicon-containing fibers according to the present subject matter.
Figure 2:
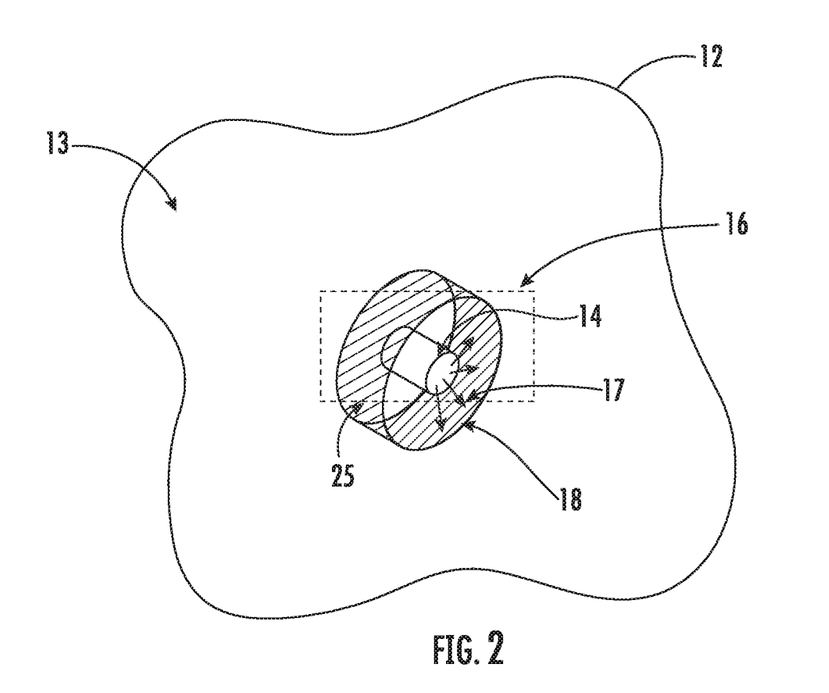
FIG. 2 shows a schematic front view of the embodiment of the vehicle safety device that employs the heat shield according to FIG. 1.

The needlepunched nonwoven that comprises silicon-containing fibers can be needlepunched together with a woven base substrate to form a heat shield material that can be cut and finished into a heat shield for use in inflator containers used to house filtration devices for use in automotive airbags that can aid in reducing distortion of the metal inflator container during use. This heat shield can have a first face that comprises needlepunched nonwoven that comprises silicon-containing fibers and a second opposite face that primarily comprises the woven base substrate. This heat shield can be easily folded and compressed and would be an ideal material for reducing the bulk and size of the heat shield mass/volume surrounding the inflator. Traditionally, nonwovens do not typically have the structural integrity to resist the impinging shockwave. However, by needling a needlepunched nonwoven comprising silicon-containing fibers to a woven base substrate a heat shield that utilizes a nonwoven can be beneficially employed. FIGS. 1 and 2 provide context of the vehicle safety device that uses such a heat shield and the environment in which the heat shield is employed. These figures are drawn to allow the viewer to see the interior of the vehicle safety device and generally understand the relationship of its components based on this written description. The embodiments are discussed in greater detail below; however, the detail illustrated in these figures is meant to be used only for purposes of illustrating the features of the invention and not as an exact detail of the invention and is not intended to be drawn to scale.

Referring to FIGS. 1 and 2, a vehicle safety device 10 is generally shown that comprises an exemplary airbag 12 that is being inflated. The airbag 12 having a heat shield 18 positioned within an interior 15 of the airbag 12 and proximate to a pyrotechnic device, or inflator, 16 having apertures 14 radially around an end of the inflator 16 for releasing gas from the inflator 16. The heat shield 18 has a first face 25 that comprises a nonwoven comprising silicon-containing fibers that encircles the end of the inflator 16 within the interior 15 of the airbag 12 such that apertures 14 are covered by the first face 25 of the heat shield 18. In particular, the vehicle safety device 10 is generally shown utilizing a heat shield 18 that comprises a nonwoven comprising silicon-containing fibers around the end of the inflator 16 covering the apertures 14 that comprises the first face and a woven base substrate that comprises a second face that faces outward toward the interior 15 of an airbag 12 that is being inflated by the gas 17 upon ignition of the inflator 16 to fill the interior 15 of an airbag 12. When a vehicle crashes, the pyrotechnic device 16 ignites sending hot gas 17 through the radially positioned apertures 14 around the end of the inflator 16 through the heat shield 18 and into the interior 15 of an airbag 12 to create the airbag cushion. The hot gas 17 initially passes through a first face of the heat shield 18 that comprises a nonwoven comprising silicon-containing fibers as the hot gas 17 forces the airbag 12 to expand and to create a cushion for the vehicle occupant. The heat shield dissipates heat from the hot gas 17 as the hot gas 17 passes through the heat shield 18.

Figure 3:
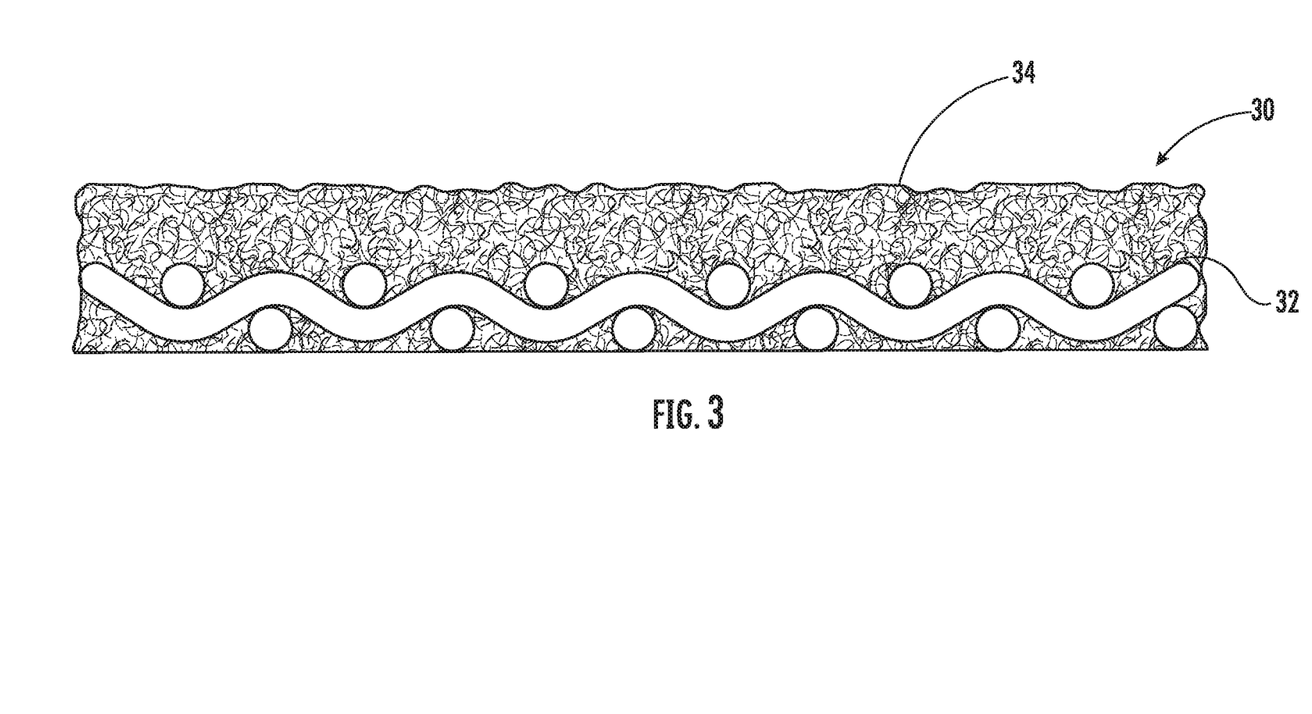
FIG. 3 illustrates a side cross-sectional view of a portion of an embodiment of a heat shield according to the present subject matter.

Thus, the heat shield 18 can be utilized as a heat shield positioned within the interior space 15 of an airbag 12 around the end of the inflator 16 positioned within the interior 15 of the airbag 12 covering the apertures 14, through which the hot gas generated by the inflator 16 will enter the airbag 12 and make initial first contact. The location can be selected to include those areas where the hot gas comes in contact with the heat shield 18 before coming in contact with the inner surface 13 of the airbag 12. Referring to FIG. 3, for example, the hot gas 17 flows through the apertures 14 and comes in contact with the heat shield 18. The gas 17 then enters the interior 15 of the airbag 12. Due to the nonwoven substrate that comprises silicon-containing fibers, the heat shield 18 is able to withstand the temperature of the gas/particulates 17 exiting the pyrotechnic device 16, allowing the gas 17 to travel into the interior space 15 of the airbag 12 causing inflation of the airbag 12 to act as a cushion for the vehicle occupant.

Due to the presence and positioning of the heat shield 18, any applied heat energy first contacts the nonwoven substrate comprising silicon-containing fibers directly to dissipate heat, which serves to protect the fabric of the airbag 12.

No matter the particular configuration of the airbag, the heat shield 18 that comprises the nonwoven comprising silicon-containing fibers can be utilized to inhibit premature deflation of the airbag caused by particular and/or hot gas burn through. The airbag material 12 can be any suitable material known in the airbag manufacturing arts, including but not limited to, a nylon fabric. The heat shield 18 can be any suitable size sufficient to delay contact between the hot gas and the inner surface of the airbag. The size and shape of the airbag 12 and, accordingly, the size and shape of the heat shield 18 and the airbag 12 will vary depending on where the airbag 12 is to be located (i.e., the front or side of the vehicle, in the drivers or passenger's seat).

Figure 4:
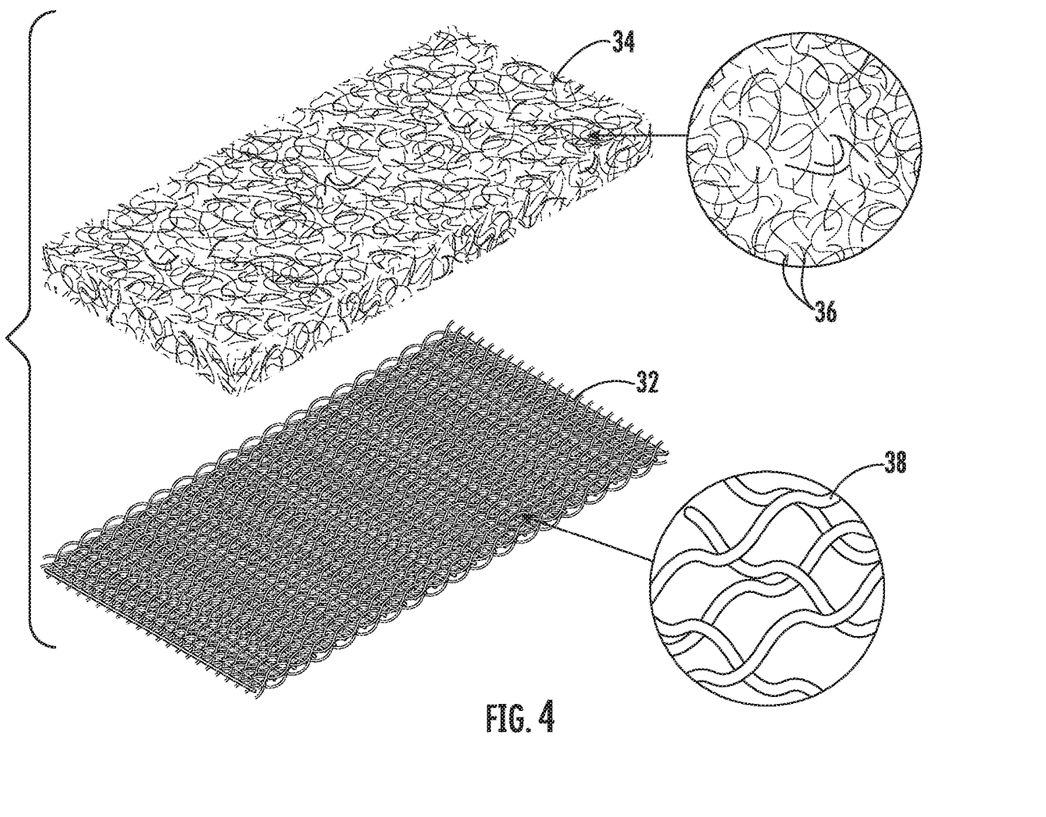
FIG. 4 illustrates a perspective view of components of an embodiment of a heat shield according to the present subject matter.
Figure 5:
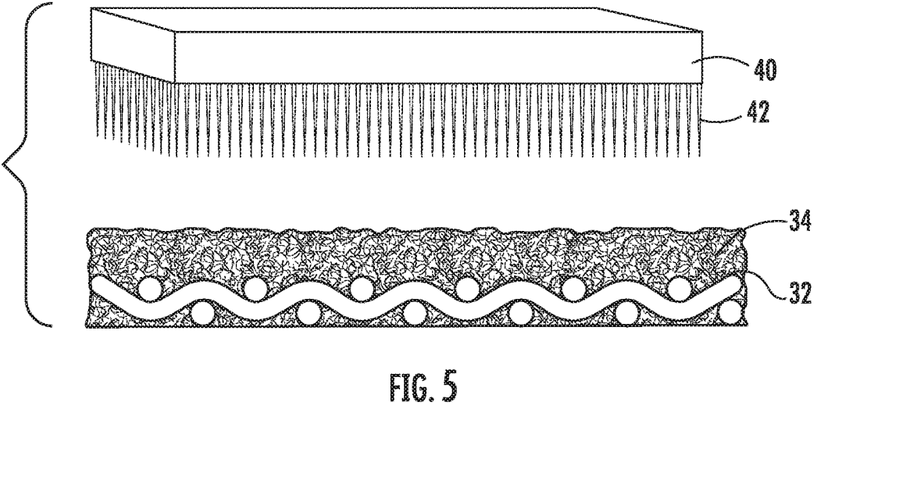
FIG. 5 illustrates a perspective cross-sectional view of the embodiment of the heat shield according to FIG. 4 in a process of joining a nonwoven substrate to a woven base substrate according to the present subject matter.

Referring to FIGS. 3-5, a portion of heat shield 30 for use in vehicle airbags is provided. The heat shield 30 comprises a woven base substrate 32 and a needlepunched nonwoven substrate 34 comprising silicon-containing fibers. As stated above, other fibers, such as polyester, polypropylene, or other suitable thermoplastic polymer fibers may also be included in the needlepunched nonwoven substrate 34. As shown in FIG. 5, the needlepunched nonwoven substrate 34 can be needlepunched to the woven base substrate 32 to form a heat shield material. As shown in FIGS. 1 and 2, the heat shield material that comprises needlepunched nonwoven substrate 34 on a first face and the woven base substrate 32 on an opposing second face can be cut, finished, formed in a heat shield such that the heat shield can be positioned within an interior of an airbag such that the needlepunched nonwoven substrate faces apertures within an inflator of the airbag.

As shown in FIG. 4, the needlepunched nonwoven substrate 34 can comprise fibers 36, such as silicon-containing fibers. In some embodiments, the needlepunched nonwoven substrate 34 can have the silicon-containing fibers comprise between about 15% and about 100% by weight of the needlepunched nonwoven substrate 34. In some embodiments, the silicon-containing fibers comprise between about 30% and about 100% by weight of the needlepunched nonwoven substrate 34. As stated above, the needlepunched nonwoven substrate 34 can comprise fibers 36 that are a blend of silicon-containing fibers and polyester fibers. In some embodiments, the silicon-containing fibers comprise between about 30% and about 50% of the needlepunched nonwoven substrate 36. In some embodiments, the silicon-containing fibers comprise silica fibers. In some embodiments, the silica fibers comprise sodium silicate. In some embodiments, the needlepunched nonwoven substrate 34 can comprise a nonwoven substrate having a weight of between about 8 oz./yd$^2$ and about 15 oz./yd$^2$.

As shown in FIG. 4, the woven base substrate 32 can comprise yarns 36, such as aromatic polyamide, or aramid, yarns. For example, the yarns 36 can comprise meta-aramid yarns and/or para-aramid yarns. In some embodiments, the yarns 36 are nylon. In some embodiments, these yarns 36 may comprise staple length fibers spun into nylon yarns or can comprise filament yarns of nylon. The woven base substrate 32 can be a light weight fabric. For example, in some embodiments, the woven base substrate can comprise a woven fabric having a weight of between about 6 oz./yd$^2$ and about 15 oz./yd$^2$. In some embodiments, the woven base substrate can comprise a nylon woven fabric having a weight of between about 6 oz./yd$^2$ and about 15 oz./yd$^2$. In some embodiments, the woven base substrate can comprise a nylon woven fabric having a weight of between about 6 oz./yd$^2$ and about 10 oz./yd$^2$.

Figure 6:
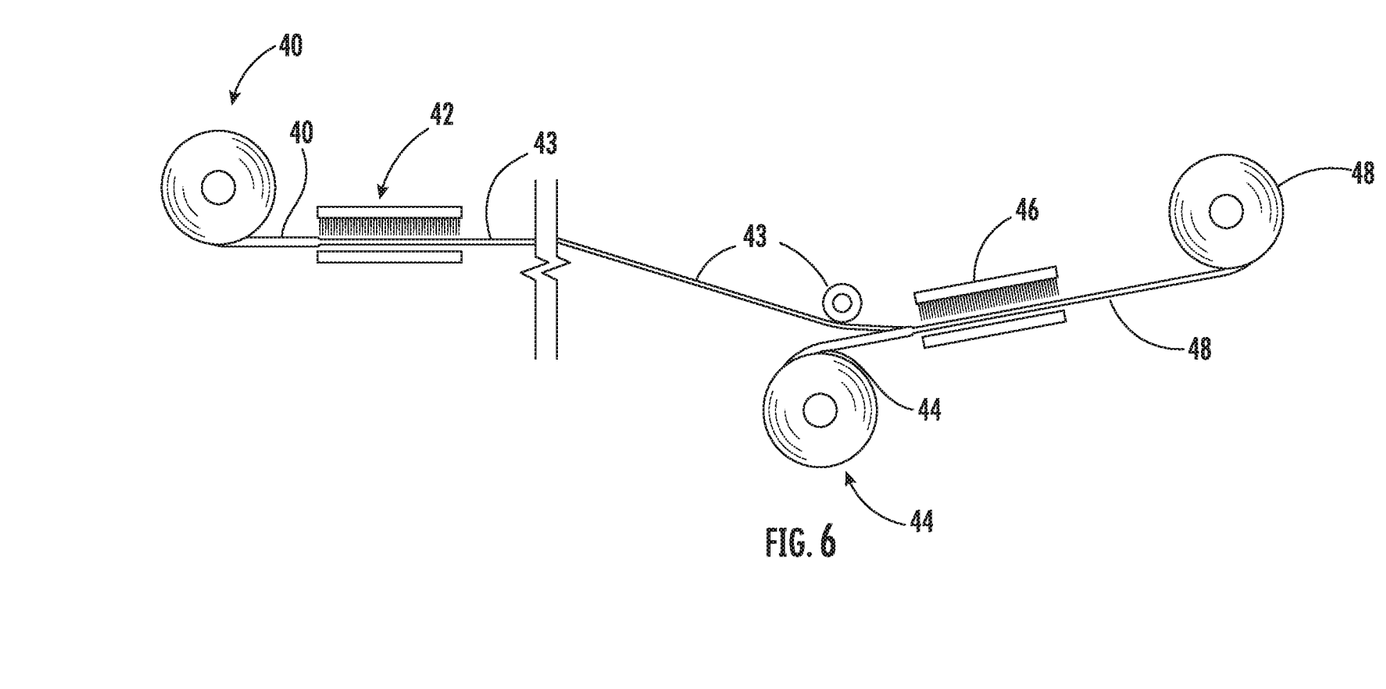
FIG. 6 illustrates a schematic view of an embodiment of a process of making a heat shield material according to the present subject matter that is used to form a heat shield.

A method of making a heat shield for use in vehicle airbags is also disclosed herein. The method can comprise making a heat shield material as shown in FIG. 6 and then cutting and finishing the heat shield material into one or more heat shields. As shown in FIG. 6, a web 40 comprising silicon-containing fibers and can, in some embodiments, also comprise other suitable thermoplastic polymer fibers, such as polyester fibers can be provided, for example, in a roll. Alternatively, the web 40 can come from a processing line that blends fibers to form the web. For example, a processing line that includes opening and carding equipment and one or more cross-lappers can be used to blend the fibers and form the web 40. The web 40 comprising the silicon-containing fibers can be needled using a needlepunching machine to form a needlepunched nonwoven substrate 43. The method can further comprise providing a woven base substrate 44. In some embodiments, the woven base substrate 44 can comprise a light weight nylon woven fabric having a weight of between about 6 oz./yd$^2$ and about 15 oz./yd$^2$. The needlepunched nonwoven substrate 43 can be aligned and positioned on top of the woven base substrate 44 and run through a needlepunching machine 46 to needle the needlepunched nonwoven substrate 43 comprising the silicon-containing fibers to the woven base substrate 44 to form a heat shield material 48. The heat shield material can then be rolled onto a roll for later use to cut and assembly the heat shield material 48 into heat shields. Alternatively, the heat shield material 48 can be processed after formation by cutting and finishing the heat shield material 48 into one or more heat shields in the processing line.

Figure 7:
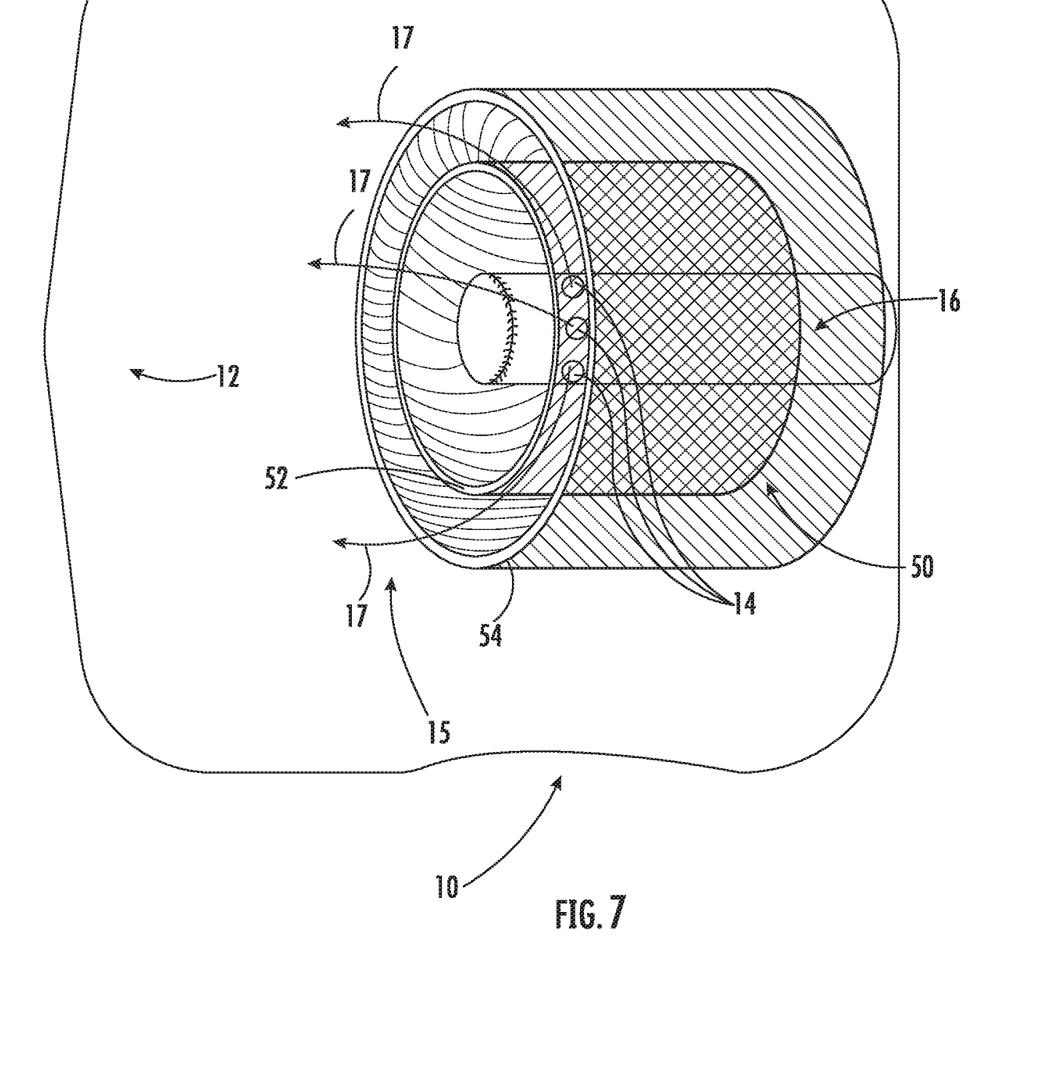
FIG. 7 illustrates a schematic perspective view of an embodiment of a vehicle safety device that employs an embodiment of a heat shield comprising a nonwoven face that comprises silicon-containing fibers according to the present subject matter.

FIG. 7 shows a vehicle safety device, generally designated 10 that can comprise an airbag 12 comprising a base fabric and forming an interior space 15. The vehicle safety device 10 can also comprise a pyrotechnic device 16 that includes apertures 14 in the end of the pyrotechnic device 16 that resides in the interior space 15 of the airbag 12. The pyrotechnic device 16 is configured to fill the interior space 15 of the airbag 12 with a gas 17 upon ignition. The vehicle safety device 10 can further comprise a heat shield 40 positioned within the interior 15 of the airbag 12 and encircling the pyrotechnic device 16 to cover the apertures 14 therein. The heat shield 40 can comprise one or more layers. In the embodiment shown, the heat shield 50 comprises a first layer 52 and a second layer 54 with each layer 52, 54 comprising a woven base substrate and a needlepunched nonwoven substrate comprising silicon-containing fibers, The needlepunched nonwoven substrate being needlepunched to the woven base substrate in each layer 52, 54 wherein the heat shield is positioned within the interior space 15 of an airbag 12 such that the needlepunched nonwoven substrates of each of the layers 52, 54 faces the apertures 14 of the pyrotechnic device 16 within the airbag 12. Each layer 52, 54 can have the same or similar properties and construction as the heat shields and heat shield materials described above.

Thus, as described above, in some embodiments, a heat shield comprising a nonwoven substrate that can comprise silicon-containing fibers ("Si") as well as other suitable polymer fibers, such as polyester fibers, that are needlepunched to an appropriate woven fabric can have the structural integrity and heat shielding properties to withstand the impinging shockwave and heat generated by the firing of an inflator and protect the inflator container in which the inflator device resides from distortion. For example, in some embodiments, the nonwovens can comprise needlepunched nonwovens. In some embodiments, the amount of PET fibers and silicon (Si)—containing fibers can vary and can depend on the expected temperature ranges created during the pyrotechnic event, the force of the impinging shockwave, the duration time at high temperatures that are expected and the composition of the fibers. For example, the Si-containing fiber, such as silica fibers, can be used to provide added heat protection. For instance, the silica fibers can be sodium silicate filament fibers or staple fibers based on silicic acid anhydrides sold under the trademark BelCoTex®. Various blends can be produced, for example, nonwoven batts or webs using about 15% silica fibers in some embodiments, about 30% silica fibers in some embodiments, and about 50% silica fibers in some embodiments depending on the optimum performance and technical requirements. The batts can be needlepunched with varying needle sizes and structures and needlepunch density to help achieve the desired strength of the nonwoven fabric.

During filter/diffuser testing of a driver inflator, a 1 mm 50% Si PET blended nonwoven disc material was inserted inside the inflator and between the outer gas spray nozzle casing and the internal gas filter/diffuser component. The nonwoven heat shield can be constrained between the filter and metal inflator cap. During the inflation event, the nonwoven heat shield is subject to shock but the normal damage to the nonwoven is minimized as the material that is constrained between the two metal surfaces. The Si heat transfer properties still permit a significant change in temperature, i.e., temperature delta. During tests, the temperature of a gas measured at 1,400° C. when entering the nonwoven can be reduced to 350/400° C. In such heat environments, the PET will likely be destroyed if subjected to sustained/prolonged high temp exposure but in the inflator event that peak exposure is for milliseconds and the heat absorption is sufficient to reduce/eliminate distortion of the metal enclosure of the inflator container of the airbag system.

As stated above, in some embodiments, a nonwoven can be constructed by needling the nonwoven into a single woven nylon substrate or by needling Si-containing fibers or Si-containing fibers and PET fibers into a single woven nylon substrate. In such embodiments, an improved structural integrity can possibly be obtained. Once such nonwoven fabrics are enclosed in the inflator enclosure, the heat absorption of Si fiber can further improve. In such heat shield embodiments, a very lightweight nylon woven can be used to aid in providing a combined damper/defuser/filter capability Such nonwoven heat shield materials can permit a reduction in the number of laminations in the conventional external wrap heat shield around the inflator and make the heat shield easy to package. In some embodiments, the needling of Si-containing fibers into PET pointbond can provide great thermal absorption properties while also providing resistance to the shockwave during the pyrotechnic event during the firing of the inflator device.

These and other modifications and variations to the present subject matter may be practiced by those of ordinary skill in the art, without departing from the spirit and scope of the present subject matter, which is more particularly set forth herein above. In addition, it should be understood the aspects of the various embodiments may be interchanged both in whole or in part. Furthermore, those of ordinary skill in the art will appreciate that the foregoing description is by way of example only, and is not intended to limit the present subject matter.

What is claimed is:

1. A heat shield for use in vehicle airbags, the heat shield comprising:
   a woven base substrate; and
   a needlepunched nonwoven substrate comprising a blend of silicon-containing fibers and polyester fibers, wherein the silicon-containing fibers comprise between about 30% and about 50% of the needlepunched nonwoven substrate, the needlepunched nonwoven being needlepunched to the woven base substrate such that, when the heat shield is positioned within an interior space of an airbag, the needlepunched nonwoven substrate faces apertures of an inflator within the airbag.

2. The heat shield according to claim 1, wherein the silicon-containing fibers comprise silica fibers.

3. The heat shield according to claim 2, wherein the silica fibers comprise sodium silicate.

4. The heat shield according to claim 1, wherein the woven base substrate comprises nylon yarns.

5. The heat shield according to claim 1, wherein the woven base substrate comprises a nylon woven fabric having a weight of between about 6 oz./yd$^2$ and about 10 oz./yd$^2$.

6. A vehicle safety device, comprising:
   an airbag comprising a base fabric and forming an interior space, wherein the airbag defines an aperture;
   a pyrotechnic device positioned within working proximity to the aperture defined in the airbag, wherein the pyrotechnic device is configured to fill the interior space of the airbag with a gas upon ignition; and
   a heat shield positioned within the interior of the airbag and encircling the pyrotechnic device to cover apertures within the pyrotechnic device, wherein the heat shield comprises:
   a woven first substrate; and
   a needlepunched nonwoven substrate comprising a blend of silicon-containing fibers and polyester fibers, wherein the silicon-containing fibers comprise between about 30% and about 50% of the needlepunched nonwoven substrate, the needlepunched nonwoven substrate being needlepunched to the woven first substrate such that, when the heat shield is positioned within the interior space of the airbag, the needlepunched nonwoven substrate faces the apertures of an inflator within the airbag.

7. The vehicle safety device according to claim 6, wherein the silicon-containing fibers comprise silica fibers.

8. The vehicle safety device according to claim 6, wherein the woven base substrate comprises nylon yarns.

9. The vehicle safety device according to claim 6, wherein the woven base substrate comprises a light weight nylon woven fabric having a weight of between about 6 oz./yd$^2$ and about 15 oz./yd$^2$.

10. A method of making a heat shield for use in vehicle airbags, the method comprising:
    providing a web comprising silicon-containing fibers and polyester fibers;
    needling the web comprising the silicon-containing fibers and the polyester fibers to form a needlepunched nonwoven substrate with the silicon-containing fibers comprise between about 30% and about 50% of the needlepunched nonwoven substrate;
    providing a woven base substrate;
    needling the needlepunched nonwoven substrate comprising the silicon-containing fibers and the polyester fibers to the woven base substrate to form a heat shield material; and
    cutting and finishing the heat shield material into one or more heat shields.

11. The method according to claim 10, wherein the step of providing a web comprise blending silicon-containing fibers and polyesters to form the web comprising the silicon-containing fibers and the polyester fibers.

12. The method according to claim 10, wherein the silicon-containing fibers comprise silica fibers.

13. The method according to claim 10, wherein the woven base substrate comprises a light weight nylon woven fabric having a weight of between about 6 oz./yd$^2$ and about 10 oz./yd$^2$.

* * * * *